United States Patent
Chappuis et al.

(10) Patent No.: US 10,856,859 B1
(45) Date of Patent: Dec. 8, 2020

(54) RETRACTOR DEVICE AND METHODS FOR USING THE SAME

(71) Applicants: James L. Chappuis, Atlanta, GA (US); John Daly, Atlanta, GA (US); Eric Grantham, Atlanta, GA (US)

(72) Inventors: James L. Chappuis, Atlanta, GA (US); John Daly, Atlanta, GA (US); Eric Grantham, Atlanta, GA (US)

( * ) Notice: Subject to any disclaimer, the term of this patent is extended or adjusted under 35 U.S.C. 154(b) by 81 days.

(21) Appl. No.: 16/173,597

(22) Filed: Oct. 29, 2018

Related U.S. Application Data (63) Continuation-in-part of application No. 29/602,894, filed on May 4, 2017, now Pat. No. Des. 832,432.

(51) Int. Cl.
*A61B 17/02* (2006.01)

(52) U.S. Cl.
CPC .......... *A61B 17/02* (2013.01); *A61B 17/0218* (2013.01)

(58) Field of Classification Search
CPC ............... A61B 17/02; A61B 17/0218; A61B 2017/0225; A61B 2017/0287
See application file for complete search history.

(56) References Cited

U.S. PATENT DOCUMENTS

| | | | |
|---|---|---|---|
| D26,282 S | 11/1896 | Sitterly | |
| 1,002,468 A | 9/1911 | Strangman | |
| 1,266,672 A | 5/1918 | Forster | |
| D151,973 S | 12/1948 | Frettoloso | |
| 3,384,077 A * | 5/1968 | Gauthier | A61B 17/0293 600/234 |
| 3,394,700 A * | 7/1968 | Yamamoto | A61B 17/0293 600/234 |
| 3,463,144 A * | 8/1969 | Hammond | A61B 17/0293 600/210 |
| 3,998,217 A * | 12/1976 | Trumbull | A61B 17/0293 600/233 |
| 4,164,285 A | 8/1979 | Dorman | |
| D252,787 S | 9/1979 | Jefferson | |
| D261,723 S | 11/1981 | Haller | |
| 4,610,243 A | 9/1986 | Ray | |
| 4,813,401 A * | 3/1989 | Grieshaber | A61B 17/02 600/226 |
| D307,376 S | 4/1990 | Kawasaki | |
| 4,995,875 A * | 2/1991 | Coes | A61B 17/02 600/210 |
| D320,658 S | 10/1991 | Quigley et al. | |
| D324,424 S | 3/1992 | Michelson | |
| D346,022 S * | 4/1994 | Quigley | D24/135 |
| D363,009 S | 10/1995 | Culp | |
| 5,743,853 A | 4/1998 | Lauderdale | |
| D401,486 S | 11/1998 | Becker | |

(Continued)

*Primary Examiner* — Kevin T Truong
*Assistant Examiner* — Tracy L Kamikawa
(74) *Attorney, Agent, or Firm* — Morris, Manning & Martin, LLP; Bryan D. Stewart (57) ABSTRACT

The present disclosure relates generally to a retractor device for allowing visible access to the surgical site. According to particular embodiments, the present retractor may include two portions: an integral arm portion at one end and a textured surface potion at the opposite end. In some embodiments, the integral arm portion may be positioned inside the body cavity of the patient to restrain and/or occlude targeted organs during surgery to allow for increased visibility of other organs and/or portions of a patient during surgical procedures.

14 Claims, 7 Drawing Sheets

(56) References Cited

U.S. PATENT DOCUMENTS

| | | | |
|---|---|---|---|
| 6,196,969 B1* | 3/2001 | Bester | A61B 17/0206 |
| | | | 600/219 |
| D500,135 S | 12/2004 | Ripich et al. | |
| D510,768 S | 10/2005 | Farley | |
| 7,137,949 B2* | 11/2006 | Scirica | A61B 17/0293 |
| | | | 600/229 |
| D689,608 S | 9/2013 | Kerstein et al. | |
| D728,110 S | 4/2015 | Corbett, III et al. | |
| 9,770,236 B2 | 9/2017 | Stauber | |
| D808,379 S | 1/2018 | Simmons | |
| 2002/0013514 A1 | 1/2002 | Brau | |
| 2017/0273677 A1 | 9/2017 | Gorek et al. | |

* cited by examiner

RETRACTOR DEVICE AND METHODS FOR USING THE SAME

CROSS REFERENCE TO RELATED APPLICATIONS

This application is a continuation-in-part application of U.S. Design patent application No. 29/602,894, filed May 4, 2017, and entitled "ALIF RETRACTOR ASSEMBLY," the disclosure of which is incorporated by reference in its entirety as if the same were fully set forth herein.

TECHNICAL FIELD

The present disclosure relates generally to a surgical retractor device.

BACKGROUND

Generally, surgical retractor devices are used in some surgical operations for holding back muscles, organs (including skin), and tissue allowing a surgeon access to, and better visibility into, a patient's body cavity during a surgical procedures. Typically, the surgeon will require a surgical incision device designed to make uniform cuts through the skin and soft tissue of the patient and a self-retaining retractor designed for a hands-free operation. The type of retractor used by the surgeon may depend on the depth of the incision, size of the patient, or other factors.

As will be understood, proper retraction of the tissue and vital organs during surgical procedures may be highly beneficial in ensuring proper exposure to the surgical site and providing protection against accidental injury to the patient due to the lack of visibility. Existing retractor systems may lack enough retraction blades or the blades may not be an optimal shape for retracting certain human organs.

Therefore, there is a long-felt but unresolved need for an improved retractor device and methods for using the same.

BRIEF SUMMARY OF THE DISCLOSURE

Briefly described, and according to one embodiment, aspects of the present disclosure generally relate to a surgical retractor for holding human organs in place, such that a surgeon may better access another organ or surgical site. In particular embodiments, retractors discussed herein may be used for anterior lumbar interbody fusion ("ALIF") procedures and are for retracting organs and allowing clear access to a surgical site (e.g., the spine). Further, according to at least one embodiment, the retractor discussed herein may be attached to a portion of a retractor system (e.g., an INTEGRA Omni-Flex™ Retractor System, an INTEGRA Omni-Tract Retractor System, or the like) via one or more attachment mechanisms. In particular embodiments, the retractor device discussed herein may include a blade that may be bent (e.g. downward into a body cavity) to hold one or more organs (e.g., a bladder) via one or more teeth, via the body of the blade, or the like.

In one embodiment, the present disclosure discusses a retractor for occluding one or more organs during surgery, the retractor including: (a) a generally flat, elongated body defining at least one opening and comprising: (i) a first end and a second end opposite the first end; (ii) an arm portion integrally formed with a textured portion, the textured portion defining the at least one opening proximate the second end; and (iii) one or more teeth located proximate the first end and integrally formed with the arm portion; (b) a support plate sized to cover the at least one opening; and (c) one or more fasteners for attaching the support plate to the elongated body.

In various embodiments, the textured portion includes one or more wave-like structures. In certain embodiments, the textured portion includes two rows of wave-like structures. In a particular embodiment, the two rows of wave-like structures are at least partially bisected by the at least one opening. In one embodiment, the one or more fasteners attach the support plate to the elongated body at a substantially flat portion of the textured portion. According to various aspects of the present disclosure, the textured portion defines four holes for receiving the one or more fasteners.

Furthermore, in various embodiments, the arm portion includes a substantially flat top surface in a particular plane. In particular embodiments, the one or more teeth each include a substantially flat top surface in the particular plane. In one embodiment, the one or more teeth protrude from the first end and are each substantially the same thickness as the arm portion of the elongated body. In certain embodiments, the one or more teeth include two teeth.

In a particular embodiment, the present disclosure discusses a retractor including: (a) a generally flat, elongated body defining at least one opening and comprising: (i) a first end and a second end opposite the first end; (ii) an arm portion comprising a substantially flat top portion in a particular plane and integrally formed with a textured portion, the textured portion defining the at least one opening proximate the second end; and (iii) at least one tooth located proximate the first end, integrally formed with the arm portion, and comprising a substantially flat top surface in the particular plane; (b) a support plate sized to cover the at least one opening; and (c) one or more fasteners for attaching the support plate to the elongated body.

In one embodiment, the one or more teeth protrude from the first end and include a first thickness. In various embodiments, the arm portion includes a second thickness; and the first thickness is equal to the second thickness. In certain embodiments, the textured portion includes one or more wave-like structures. In a particular embodiment, the textured portion includes one or more of a rough top and/or bottom surface, a substantially flat surface, a wave-like structure, and grooves. In some embodiments, the textured portion includes two rows of wave-like structures. According to various aspects of the present disclosure, the two rows of wave-like structures are at least partially bisected by the at least one opening. In one embodiment, the one or more fasteners attach the support plate to the elongated body at a substantially flat portion of the textured portion. In particular embodiments, the textured portion defines four holes for receiving the one or more fasteners.

In one embodiment, the present disclosure discusses a retractor including: (a) a generally flat, elongated body defining at least one opening and comprising: (i) a first end and a second end opposite the first end; (ii) an arm portion comprising a substantially flat top portion in a particular plane; (iii) a textured portion integrally formed with the arm portion, the textured portion defining the at least one opening proximate the second end; (iv) a substantially malleable material such that a user can bend the arm portion to approximately 90 degrees while the textured portion is in a fixed position; and (v) at least one tooth located proximate the first end, the at least one tooth integrally formed with the arm portion and comprising a substantially flat top surface in the particular plane; (b) a support plate sized to cover the at least one opening; and (c) one or more fasteners for attaching the support plate to the elongated body, wherein the support plate and the one or more fasteners substantially hold the textured portion in the fixed position during a surgical procedure.

These and other aspects, features, and benefits of the claimed embodiment(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended. Any alterations and further modifications of the described or illustrated embodiments and any further applications of the principles of the disclosure as illustrated therein are contemplated as would normally occur to one skilled in the art to which the disclosure relates. All limitations of the scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

According to particular embodiments, the present retractor may include two portions: an integral arm portion at one end, for holding patient organs in place, and a textured surface potion at the opposite end for connecting the present retractor to a docketing system. The surgical retractor discussed herein may be used in a wide range of surgical procedures. The retractor may be configured for use in both open and minimally invasive surgical procedures (e.g. orthopedic or the like). In some embodiments, a first end of the retractor may be positioned inside a body cavity of a patient and may hold target organs (e.g. bladder) in a particular position.

In various embodiments, the retractor may be configured to engage with a surgical retractor docking system commonly used during surgical procedures (e.g., general, urological, orthopedic, etc.) via the textured surface portion. Generally, such surgical retractor docking systems may include a sterile field post and a frame structure of any suitable shape (e.g., halo or semi-circular) that includes support arms and retractor blade attachments. In various embodiments, the surgical retractor docking system may be generally assembled by first securing the field post by way of a universal clamp to a surgical table. In continuing with the embodiment, the frame structure may be adjustably clamped to the field post allowing the frame to be positioned above the patient. In one or more embodiments, the support arms of the frame may be independently positioned in selected positions required by the surgical site.

In some embodiments, the retractor described herein attaches to a surgical retractor docking system frame structure (or other suitable location) via the textured surface portion. The retractor discussed herein may be coupled directly to the universal docking system by any suitable fastener (e.g. screws, bolts, etc.) and may be positioned in any suitable manner required for the surgical site. In at least one embodiment, a surgical retractor docketing system may include components for receiving tools such as the retractor discussed herein for holding back and/or maintaining the positions of various organs (e.g. bladder) and the present retractor may be attached to the surgical retractor docking system via the components of the surgical retractor docking system.

For example, consider a scenario involving a Lumbosacral joint (L5-S1) fusion surgery that may be performed by a surgeon as a treatment for refractory lower back pain. One approach for L5-S1 surgery is Anterior Lumbar Interbody Fusion (ALIF), which is a minimally invasive approach. Although this technique has several standardized surgical techniques and procedures, including use of a docking system, challenges during surgery still remain (e.g. retained retraction of patient internal organs). Continuing with this example, the surgeon may find it difficult to hold back various organs (e.g. bladder) and may require a nurse to hold back the bladder during surgery for increased visibility to the surgical site. In this example, a retractor device, such as the one disclosed herein, may be attached to a docketing system and hold a patient's bladder (or other organs) in a particular position, instead of a nurse or other surgical assistant.

Exemplary Embodiments

Figure 1:
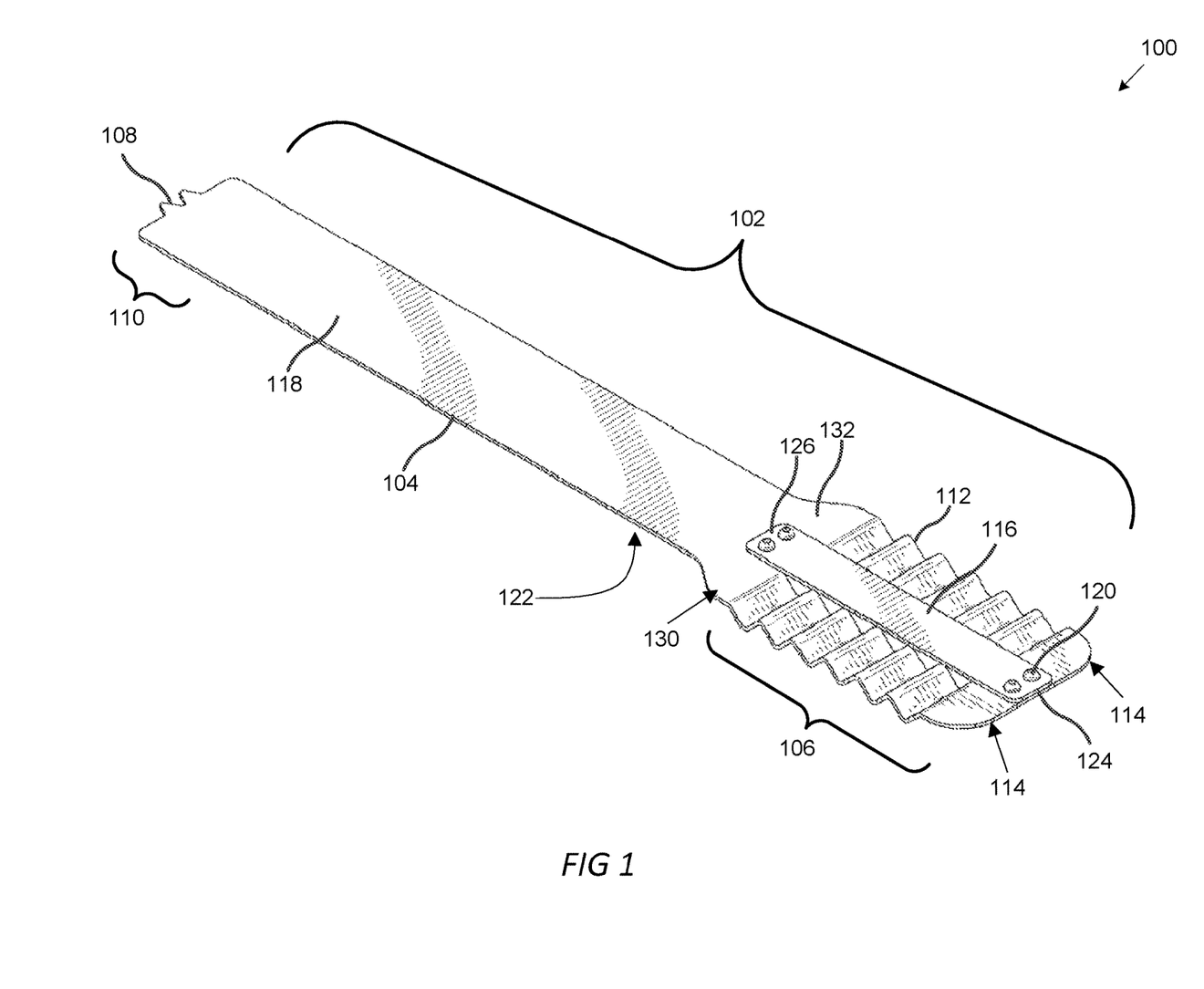
FIG. 1 is a perspective view of an exemplary retractor, according to one embodiment of the present disclosure.

Referring now to the figures, for the purposes of example and explanation of the fundamental processes and components of the current disclosure, reference is made to FIG. 1, which illustrates an exemplary retractor 100, according to one embodiment of the present disclosure.

As shown in the embodiment of FIG. 1, the retractor 100 includes an elongated body 102 with two portions: an integral arm 104 (which may also be referred to herein as a "blade") at one end and a textured gripping portion 106 at the opposite end. In exemplary use cases, the retractor 100 may be affixed to a retractor system frame (not shown) via the textured gripping portion 106 and the integral arm 104 may be manipulated (e.g., bent) to pass into a patient's body cavity and hold one or more organs in a particular position.

In some embodiments, the integral arm 104 is generally flat and substantially smooth across a top surface 118 and bottom surface 122. In the embodiment shown, the integral arm 104 is generally rectangular in shape. In some embodiments, the integral arm 104 may be any suitable shape (e.g. arc, cylinder, rod, tubular, etc.).

In at least one embodiment, the integral arm 104 may have more or more teeth 108 projecting from a first end 110 of the integral arm 104. In some embodiments, the teeth 108 may extend along an entire length of the first end 110. In further embodiments, the teeth 108 may extend along a portion of the length of the first end 110. In still further embodiments, the retractor 100 may include any suitable number of teeth (e.g., two as shown in FIG. 1, three, four, five, etc.).

In particular embodiments, the teeth 108 may be of any suitable shape, including, but not limited to: substantially pyramid-shaped, substantially spike-shaped, substantially curved (e.g., from a base of the tooth to the tip/point), or any combination thereof. In various embodiments, there is a transitional area 130 that is sloped from the proximal end 132 of the integral arm 104 to the textured gripping portion 106.

In various embodiments, the retractor 100 includes an elongated body 102 with an integral arm 104 at one end and a textured portion 106 at the other end. In some embodiments, the textured portion 106 may include texturing such as ridges, grooves and/or waved-liked wedges 112 of varying heights, widths, and depths. In one or more embodiments, the wedges 112 of the textured gripping portion 106 may be designed for any suitable height, width and depth to operably fit the frame of a retractor docking system and may allow for lateral adjustment of the retractor 100 based on the surgical site.

In some embodiments, the textured portion 106 may include a varying number of wedges 112 where each wedge may include any suitable angle or may be separated by any suitable distance. As shown in the present embodiment, the textured portion 106 includes two wedged columns 114 separated by a support plate 116. As will be understood, the retractor 100 may include any number of wedged columns.

In various embodiments, the retractor 100 includes a support plate, beam and/or spine 116 that is substantially the same length of the textured gripping portion 106 for allowing the plate 116 to be affixed to the proximal 126 and distal 124 end of the textured gripping portion 106. In some embodiments, the support plate 116 may have a flat and substantially smooth surface. In some embodiments, the support plate 116 may be any suitable size/shape. In various embodiments, the support plate 116 is substantially rectangular in shape and includes one or more holes (not shown). In various embodiments the support plate 116 may connect to one or more holes (not shown) on the textured gripping portion 106. As will be understood from discussion herein, the support plate 116 is substantially parallel to the textured gripping portion 106 and may be operatively (or removeably) attached to the textured gripping portion 106 via any suitable fastener 120 (e.g., bolts, screw, rivet, etc.). In some embodiments, the textured surface 106 may include one or more support plates 116 affixed to the proximal 126 and distal 124 ends. In one embodiment, the one or more support plates 116 may be affixed to the textured gripping portion 106 as to form a configuration that may be v-shaped, crossed-shaped, x-shaped and/or parallel, etc.

As will be understood from discussions herein, in various embodiments, the retractor 100 and associated components may be made of metal, steel or any other suitable materials. In particular embodiments, the retractor 100 may be made of any suitable malleable metals to allow for flexibility.

In various embodiments, the retractor 100 may be any suitable shape (e.g. generally linear and/or u-shaped). In some embodiments, the retractor 100 includes varying widths, depths, and thickness as to allow for suitable insertion into the surgical incision of a patient undergoing a surgical procedure.

Continuing with FIG. 1, in various embodiments, the support plate 116 may provide a way to either engage or disengage the retractor 100 directly to the frame of a commonly used retractor docketing system (not shown). Generally, there may be space between the support plate 116 and the textured gripping portion 106. In some embodiments, the retractor 100 is connected directly to the frame of the retractor docketing system by removing fasteners 120 and removing the support plate 116 and positioning a portion of the frame between the support plate 116 and the textured gripping portion 106, then reinserting and/or tightening the fasteners 120.

In some embodiments, the fasteners 120 may be any suitable fasteners, such as, for example, screws, bolts (with or without nuts), adhesives, etc. The fasteners 120 may be of any suitable length as to allow for the secure attachment of the retractor 100 to the frame of a retractor docketing system. In at least one embodiment, the support plate 116 includes removable fasteners at one end only and the opposing end is integrally formed with or otherwise attached to the textured gripping portion 106 (for example, by welding).

Figure 2:
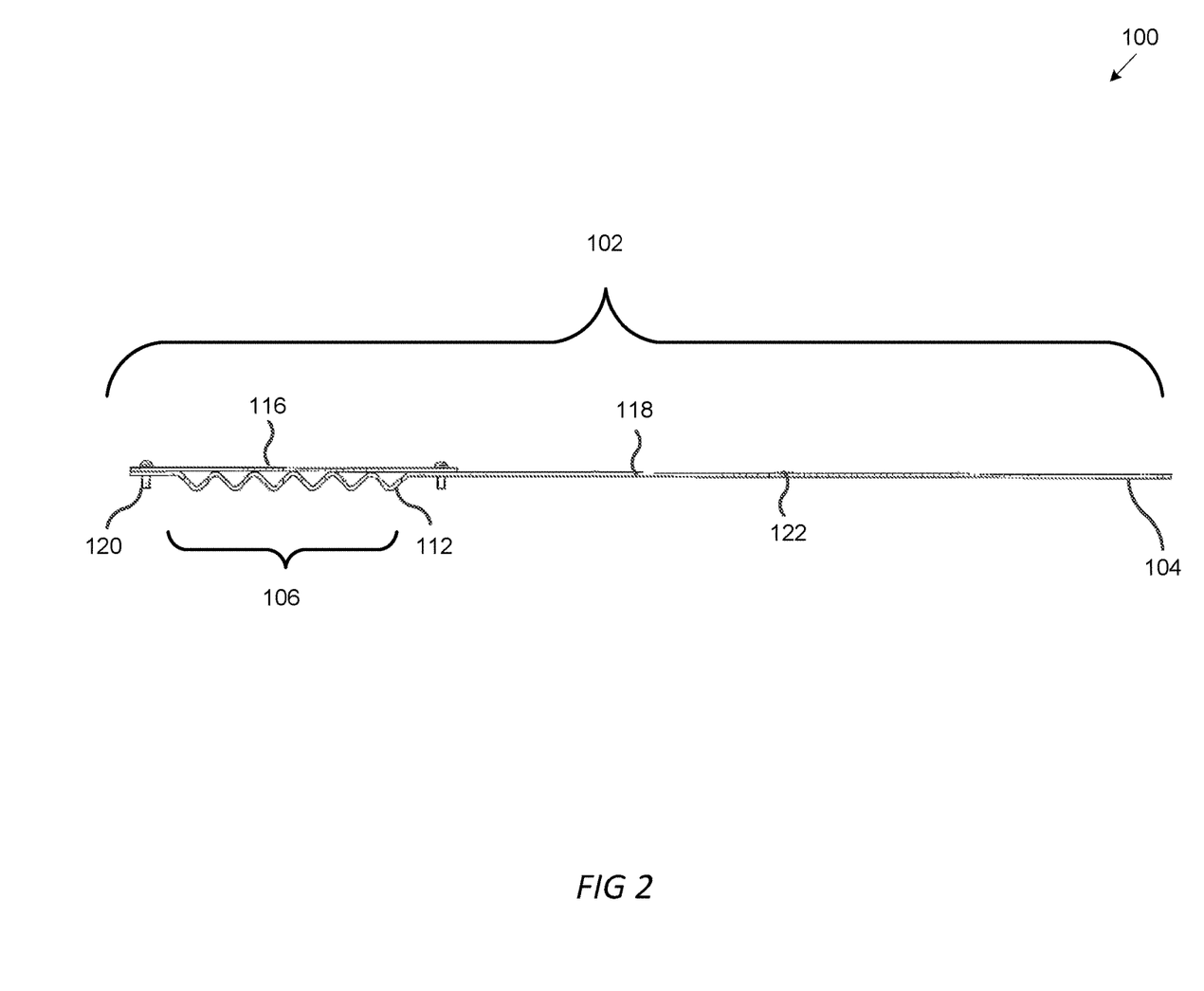
FIG. 2 is a left side view of an exemplary retractor, according to one embodiment of the present disclosure.

FIG. 2 is a left side view of an exemplary retractor 100, according to one embodiment of the present disclosure. In various embodiments, the retractor 100 may include an elongated body 102 with an integral arm 104 at one end and a textured gripping portion 106 at the other end. As shown in FIG. 2, the integral arm 104 is substantially flat and has substantially smooth top 118 and bottom 122 surfaces.

In various embodiments, the retractor 100 includes a textured gripping portion 106 with a support plate 116. In at least one embodiment, the support plate 116 is substantially parallel and operatively attached to the textured gripping portion 106 via a plurality of fasteners 120. In some embodiments, the textured gripping portion 106 may include a plurality of ridged or waved-liked wedges 112.

As discussed herein, the retractor 100 may be operatively connected to a support frame via the textured gripping portion 106 and the support plate 106. In at least one embodiment, the retractor 100 is operatively connected to the support frame by removing some (or all) of the fasteners 120 and positioning the retractor 100 such that a suitable portion of the support frame is positioned along one of the wedges 112. In these embodiments (and others), the support plate 116 is positioned above the portion of the support frame, which may be resting on or in contact with the wedges 112, and attached to the textured gripping portion 106 via the fasters 120, thereby securing the retractor 100 to the support frame.

Figure 3:
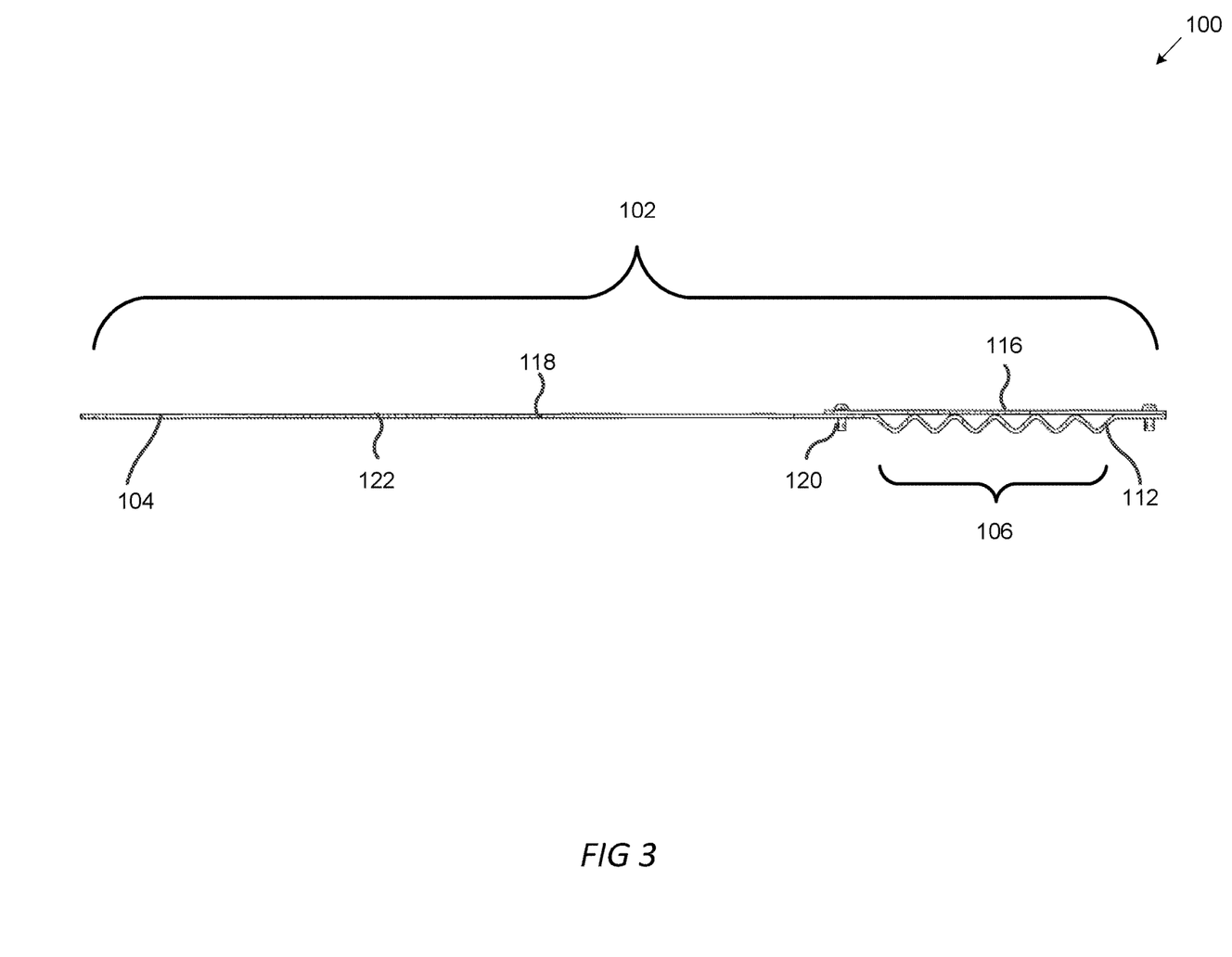
FIG. 3 is a right side view of an exemplary retractor, according to one embodiment of the present disclosure.

FIG. 3 is a right side view of an exemplary retractor 100, according to one embodiment of the present disclosure. In one embodiment, the components of this side view of the retractor 100 are substantially similar to those described in association with FIG. 2.

Figure 4:
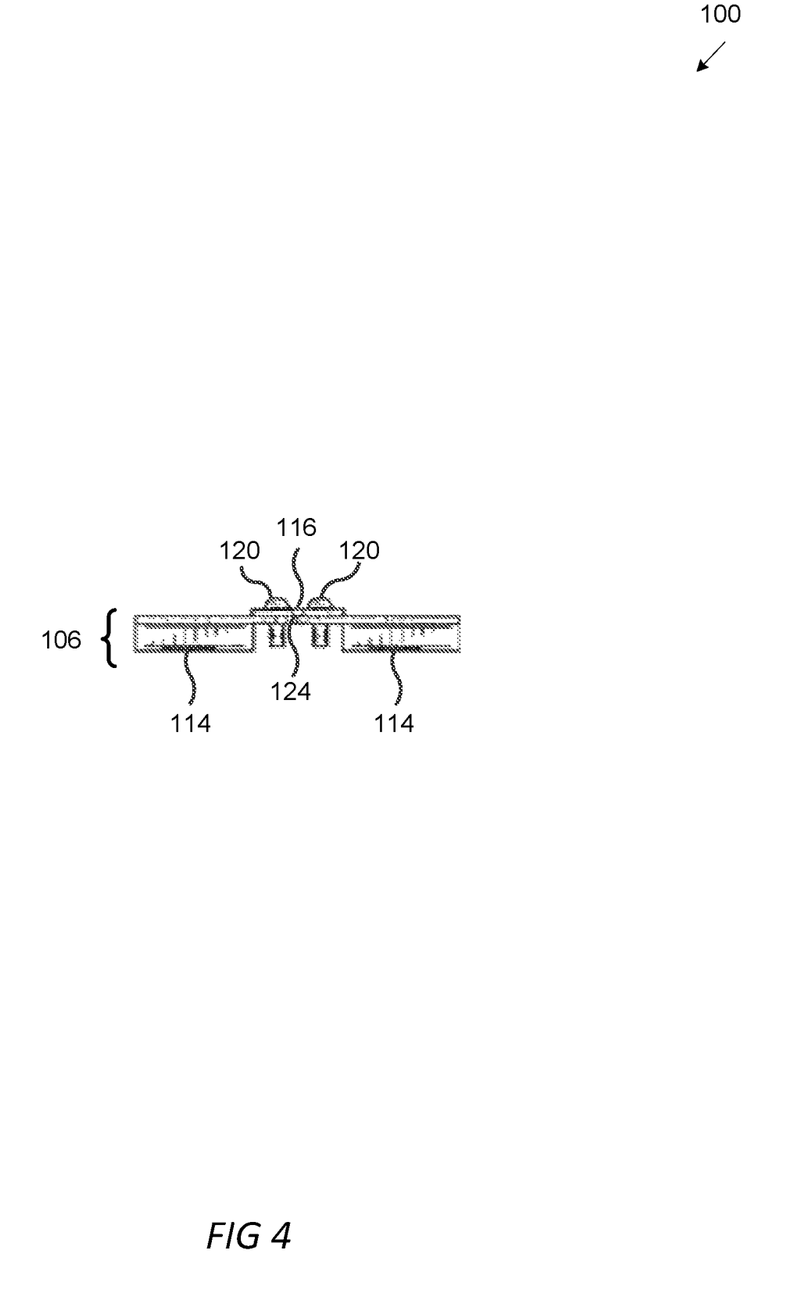
FIG. 4 is an end view of an exemplary retractor, according to one embodiment of the present disclosure.

FIG. 4 is an end view of an exemplary retractor 100, according to one embodiment of the present disclosure. In various embodiments, the retractor 100 includes a textured gripping portion 106. In some embodiments, the textured gripping portion 106 may include ridged or waved-liked wedges (not shown) and two wedged columns 114.

In various embodiments, the retractor 100 includes a support plate 116 that detachably connects to the textured gripping portion 106. The support plate 116 may be detachably connected via any suitable fastener 120 to the textured gripping portion 106.

As show in the embodiment of FIG. 3, the retractor 106 and support plate 116 are relatively flat and the textured gripping portion 106 includes one or more wedges (or other suitable protrusions) protruding downwardly from a surface of the textured gripping portion 106 in one or more columns 114.

Figure 5:
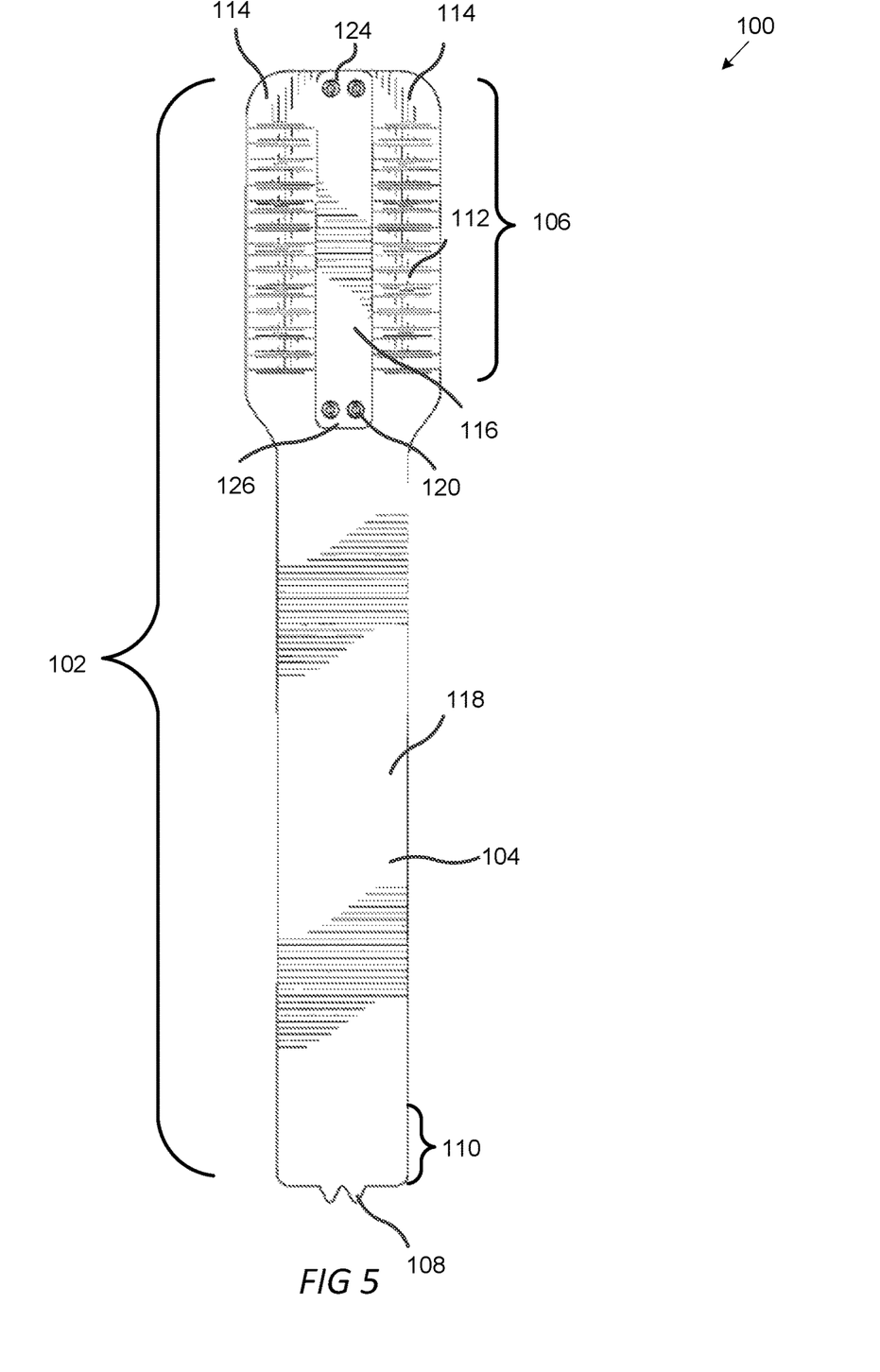
FIG. 5 is a top view of an exemplary retractor, according to one embodiment of the present disclosure.

Turning now to FIG. 5, a top view of an exemplary retractor 100 is shown, according to one embodiment of the present disclosure. In various embodiments, the retractor 100 may include an elongated body 102 with an integral arm 104 at one end and a textured gripping portion 106 at the opposite end. In some embodiments, the top surface 118 may be substantially smooth and generally flat.

In various embodiments, the retractor 100 includes an integral arm 104 that may have a plurality of teeth 108 near the first end 110. In some embodiments, the teeth 108 may extend along the length of the first end 110 and may be integrally formed with top surface 118 (e.g., top surface 118 transitions to the plurality of teeth 108, which have a top surface in the same plane as the top surface 118). As discussed herein, the plurality of teeth 108 may be of any suitable shape (e.g., pointed, rounded, generally rectangular, etc.).

In various embodiments, the retractor 100 includes a textured gripping portion 106. In some embodiments, the textured gripping portion 106 may include ridged or waved-liked wedges 112 of varying heights, widths and depths. As shown in the present embodiment, the textured gripping portion 106 may include two wedged columns 114. In one or more embodiments, the wedges 112 of the textured gripping portion 106 may be constructed to perform a gripping action thereby preventing dislodgement of the retractor 100 from the frame of the retractor docking system (not shown).

In various embodiments, the retractor 100 includes a support plate 116 that may extend parallel to the textured gripping portion 106 and extends from a first end 124 to the second end 126 of the textured surface. In particular embodiments, the support plate 116 is detachably connected to the first end 124 and second end 126 of the textured gripping portion 106 by one or more fasters 120.

Figure 6:
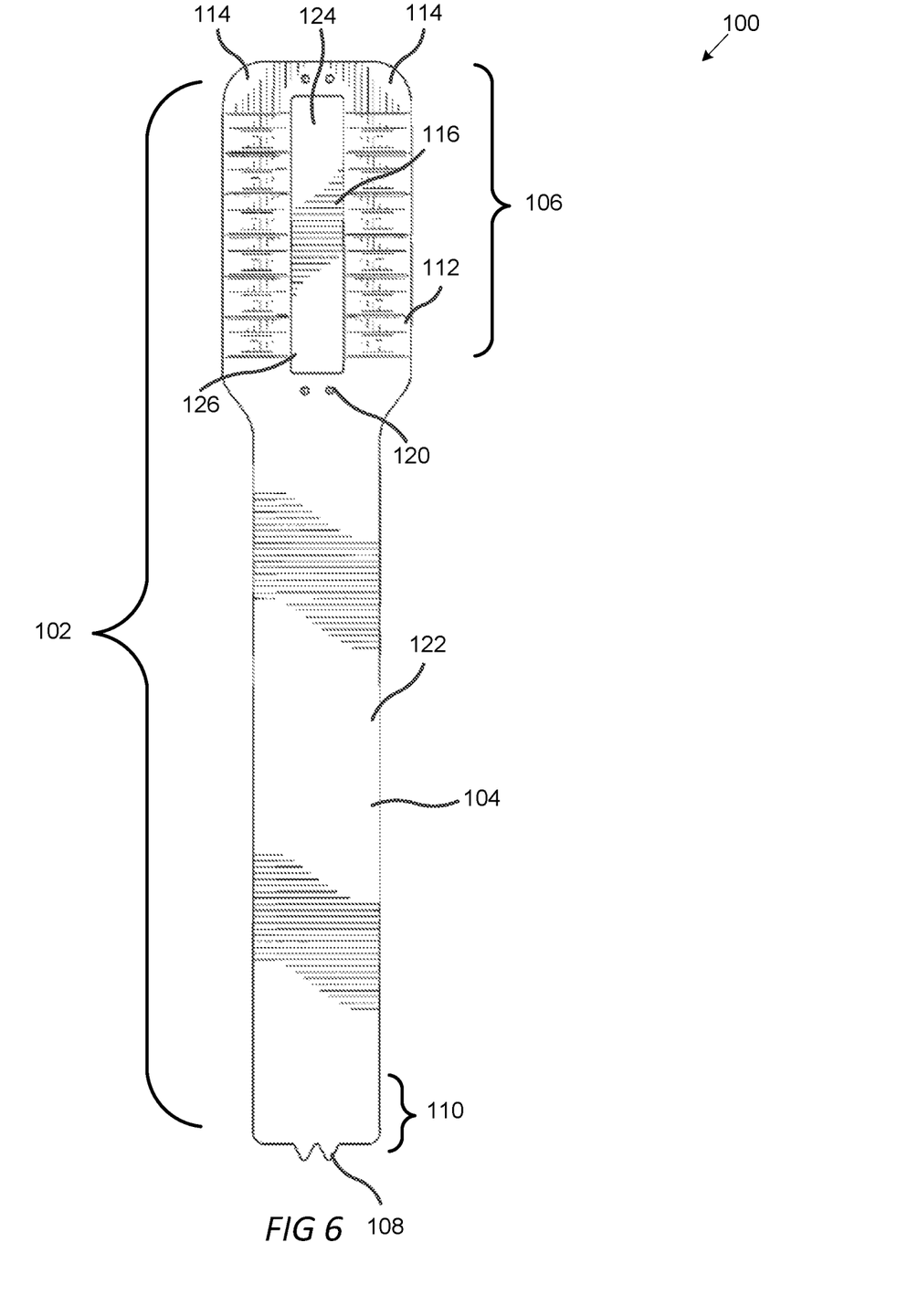
FIG. 6 is a bottom view of an exemplary retractor, according to one embodiment of the present disclosure.

FIG. 6 is a bottom view of an exemplary retractor 100, according to one embodiment of the present disclosure. In various embodiments, the retractor 100 may include an elongated body 102 with an integral arm 104 at one end and a textured gripping portion 106 at the opposite end. In some embodiments, the bottom surface 122 may be substantially smooth and generally flat.

As shown in FIG. 6, the support plate 126 covers an opening formed in the textured gripping portion 106. As will be understood, the opening may be any suitable size and shape. In at least one embodiment, the support plate 126 is substantially the same size and shape of the opening and extending beyound to particular ends of the opening such that the support plate 116 can be attached to the texture gripping portion 106 via the fasteners 120.

Figure 7:
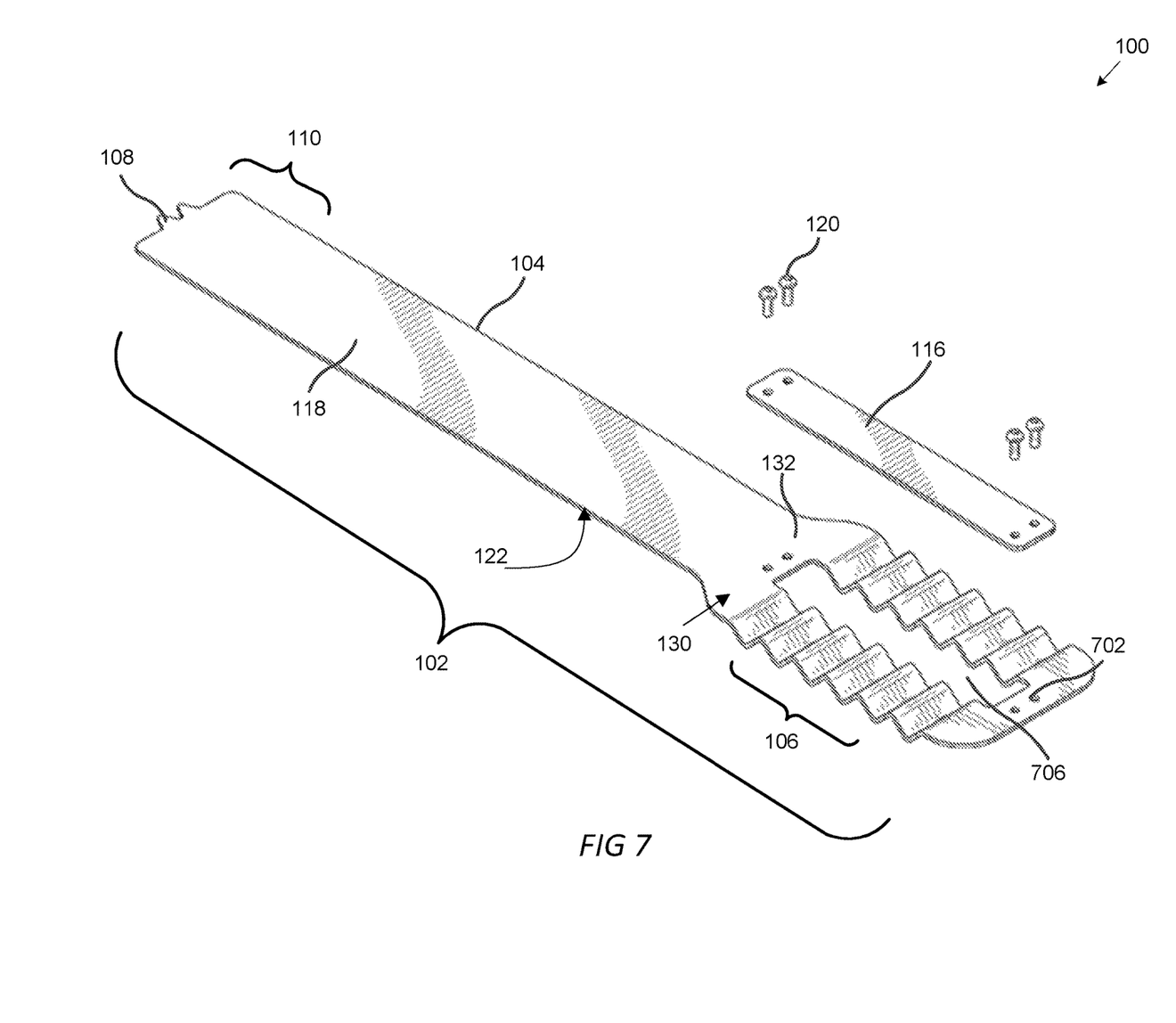
FIG. 7 is an exploded view of an exemplary retractor, according to one embodiment of the present disclosure.

FIG. 7 is an exploded view of an exemplary retractor 100, according to one embodiment of the present disclosure. In various embodiments, the retractor 100 may include an elongated body 102 with an integral arm 104 at one end and a textured gripping portion 106 at the opposite end. In some embodiments, the top surface 118 and bottom 122 surfaces may be substantially smooth and generally flat.

In various embodiments, the retractor 100 may include an integral arm 104 that may have a first end 110 fabricated with multiple projecting teeth 108. In some embodiments, the teeth 108 may extend along the length of the first end 110 and may be of any suitable size, width, depth and/or height. In some embodiments, the first end 110 of the integral arm 104 of the retractor 100 may be positioned inside the body cavity of the patient and may compress upon targeted organs (e.g. bladder) to restrain and/or occlude targeted organs during surgery to allow increased visibility to the spine or the like.

In various embodiments, the textured gripping portion 106 may include one or more holes 702 for attaching to the support plate 116 using fasteners 120 to the retractor 100. In some embodiments, the frame of the docketing system may be positioned between the support plate 116 and textured gripping portion 106.

In one embodiment, the holes 702 may allow for various support plate configurations (e.g. v-shaped, crossed-shaped, x-shaped, parallel, etc.) to be used. In some embodiments, the textured gripping portion 106 may further include a cutout or opening 706. In an embodiment shown in FIG. 7, an opening 706 is semi-rectangular in shape and may be of any suitable dimension. In one embodiment, the support plate 116 may be attached and substantially extend long the same length of the textured gripping portion 106.

Exemplary Use Case

As will be understood, the retractor 100 may be used in any suitable way. For example, continuing with the embodiment shown in FIG. 7, the retractor 100 is operatively connected to a frame via the support plate 116, textured gripping portion 106, and fasteners 120. A portion of the frame (not shown) is positioned between the support plate 116 and textured gripping portion 106 and the fasteners 120 fix each of the ends of the support plate 116 to the textured gripping surface portion 106 of the retractor 100. In at least one embodiment, when the retractor 100 is operatively connected to a frame, the support plate 116 and/or the textured gripping portion 106 may bend or bow around a portion of the frame between the support plate 116 and the textured gripping portion 106.

In one or more embodiments, once the retractor 100 is connected to a frame, the integral arm 104 may be bent or curved into a body cavity such that occludes a particular organ, such as a patient's bladder (or any other organ). In at least one embodiment, the plurality of teeth 108 may engage a portion of the patient (e.g., the spine or another boney structure) to hold the integral arm 104 in the bent or curved position.

Alternate Embodiments/Additional Features

In various embodiments, the retractor 100 may include any suitable lighting component (e.g. fiber-optic or the like thereof). In one or more embodiments, the lighting component may be affixed to the retractor 100 in any suitable fashion such as to provide better visualization during surgery.

In at least one embodiment, a retractor may include a malleable material, such that when a portion of the device is bent or otherwise manipulated into a different position, the device substantially stays in the different position. As an example, the integral arm 104 shown in FIG. 7 is bent downward into a patient body cavity and, in this example, the integral arm 104 stays in the bent downward position without any additional fixtures and with or without the plurality of teeth 108.

As will be understood from discussions herein, a retractor may include any suitable number of teeth or protrusions (e.g., teeth 108). In at least one embodiment, the retractor includes a singular tooth or protrusion at an end of the retractor for interacting with one or more patient organs (e.g., holding the retractor in a particular position).

CONCLUSION

The embodiments were chosen and described in order to explain the principles of the claimed disclosure and their practical application so as to enable others skilled in the art to utilize the disclosure and various embodiments and with various modifications as are suited to the particular use contemplated. Alternative embodiments will become apparent to those skilled in the art to which the claimed disclosure pertain without departing from their spirit and scope. Accordingly, the scope of the claimed disclosure(s) is defined by the appended claims rather than the foregoing description and the exemplary embodiments described therein.

What is claimed is:

1. A retractor for occluding one or more organs during surgery, the retractor comprising:
   an elongated body defining at least one opening and comprising:
      a first end and a second end opposite the first end;
      an arm portion, having a substantially flat top surface in a top plane and a substantially flat bottom surface in a bottom plane, integrally formed with a textured portion;
      the textured portion defining the at least one opening proximate the second end and comprising two rows of wave-like structures, wherein each wave-like structure of the two rows of wave-like structures extends from the top plane through the bottom plane such that a crest of each wave-like structure resides in the top plane and a trough of each wave-like structure extends below the bottom plane, wherein the two rows of wave-like structures are at least partially separated by the at least one opening; and
      one or more teeth extending from the first end and integrally formed with the arm portion, wherein each of the one or more teeth is substantially triangular, comprising a top tooth surface in the top plane and a bottom tooth surface in the bottom plane; and
   a support plate sized to cover the at least one opening, wherein the support plate has a substantially flat plate top surface parallel to the top plane and the bottom plane; and
   one or more fasteners for attaching the support plate to the elongated body.

2. The retractor of claim 1, wherein the one or more fasteners attach the support plate to the elongated body at a substantially flat portion of the textured portion.

3. The retractor of claim 2, wherein the textured portion defines four holes for receiving the one or more fasteners.

4. The retractor of claim 1, wherein the one or more teeth extend from the first end and are each substantially the same thickness as the arm portion of the elongated body.

5. The retractor of claim 4, wherein the one or more teeth comprise two teeth.

6. The retractor of claim 1, wherein:
   a first tooth of the one or more teeth extends from the arm portion at a particular location and forms a point; and
   the top tooth surface and the bottom tooth surface of the first tooth are flat from the particular location to the point.

7. The retractor of claim 1, wherein the support plate is substantially the same length as the textured portion.

8. The retractor of claim 7, wherein the support plate is further sized to cover the entirety of the at least one opening.

9. The retractor of claim 1, wherein the at least one opening is substantially rectangular.

10. A retractor comprising:
    an elongated body defining at least one opening and comprising:
       a first end and a second end opposite the first end;
       a flat arm portion comprising a substantially flat top portion in a top plane and a substantially flat bottom portion in a bottom plane, a first thickness, and integrally formed with a textured portion, the textured portion defining the at least one opening proximate the second end and comprising two rows of wave-like structures, wherein each wave-like structure of the two rows of wave-like structures extends from the top plane through the bottom plane such that a crest of each wave-like structure resides in the top plane and a trough of each wave-like structure extends below the bottom plane, wherein the two rows of wave-like structures are at least partially separated by the at least one opening; and
       one or more teeth extending from the first end, integrally formed with the arm portion, and each comprising:
          a substantially flat top surface in the top plane;
          a second thickness equal to the first thickness of the flat arm portion; and
          a substantially triangular shape;
    a support plate sized to cover the at least one opening, wherein the support plate has a substantially flat top surface parallel to the top plane; and
    one or more fasteners for attaching the support plate to the elongated body.

11. The retractor of claim 10, wherein the one or more fasteners attach the support plate to the elongated body at a substantially flat portion of the textured portion.

12. The retractor of claim 11, wherein the textured portion defines four holes for receiving the one or more fasteners.

13. A retractor comprising:
    an elongated body defining at least one opening and comprising:
       a first end and a second end opposite the first end;
       an arm portion comprising a substantially flat top portion in a top plane and a substantially flat bottom portion in a bottom plane;
       a textured portion integrally formed with the arm portion, the textured portion defining the at least one opening proximate the second end, the textured portion comprising two rows of wave-like structures, wherein each wave-like structure of the two rows of wave-like structures extends from the top plane through the bottom plane such that a crest of each wave-like structure resides in the top plane and a trough of each wave-like structure extends below the bottom plane, wherein the two rows of wave-like structures are at least partially separated by the at least one opening;

a substantially malleable material such that a user can bend the arm portion to approximately 90 degrees while the textured portion is operatively connected to a frame in a fixed position; and at least one tooth extending from the first end, the at least one tooth integrally formed with the arm portion and comprising a substantially flat top surface in the top plane wherein the at least one tooth is substantially triangular;

a support plate sized to cover the at least one opening, wherein the support plate has a substantially flat top surface in a plane parallel to the top plane; and one or more fasteners for attaching the support plate to the elongated body, wherein the support plate and the one or more fasteners substantially hold the textured portion in the fixed position during a surgical procedure.

14. The retractor of claim 13, further comprising a lighting component affixed to the elongated body.

\* \* \* \* \*